(12) United States Patent
Reusch

(10) Patent No.: US 6,602,398 B1
(45) Date of Patent: Aug. 5, 2003

(54) ASSAY METHOD USING POLYHYDROXYBUTYRATE AND POLYPHOSPHATE MEMBRANES WITH CHANNELS

(76) Inventor: Rosetta N. Reusch, 3940 Binghampton Dr., Okemos, MI (US) 48864

( * ) Notice: Subject to any disclaimer, the term of this patent is extended or adjusted under 35 U.S.C. 154(b) by 0 days.

(21) Appl. No.: 08/615,713

(22) Filed: Mar. 13, 1996

Related U.S. Application Data

(62) Division of application No. 08/317,204, filed on Oct. 3, 1994, now Pat. No. 5,585,249.

(51) Int. Cl.$^7$ ............................................. G01N 27/327
(52) U.S. Cl. ................................. 205/777.5; 204/403.01
(58) Field of Search ................... 436/829, 71; 514/143; 424/450, 1.21, 417, 424, 498; 252/312; 435/29, 285.1, 285.2, 285.3; 475/30; 264/4.1, 4.32; 428/402.2; 204/193, 194, 403, 409, 403.01, 777.5

(56) References Cited

U.S. PATENT DOCUMENTS

| | | | | |
|---|---|---|---|---|
| 4,661,442 A | * | 4/1987 | Lukens | ........................... 435/4 |
| 4,784,737 A | * | 11/1988 | Ray et al. | ................. 204/180.1 |
| 5,512,295 A | * | 4/1996 | Kornberg et al. | ............ 424/450 |

FOREIGN PATENT DOCUMENTS

| | | | |
|---|---|---|---|
| EP | 594282 | * | 4/1994 |
| GB | 2228635 | * | 8/1990 |
| JP | 363152972 | * | 6/1988 |

OTHER PUBLICATIONS

Karen Hopkin ("Novel Calcium Ion Channel is a Pore Without Protein," The Journal of NIH Research, Nov. 1997, vol. 5, pp. 25–2).*
Das et al. ("Proof for the nonproteinaceous calcium–selective channel in Escherichia coli by total synthesis from (R)–3–hydroxybutanoic acid and inorganic polyphosphate," Proc. Nat'l acad. Sci. USA, vol. 94, pp. 9075–9079, Aug. 1997).*
Reusch et al. ("Putative structure and functions of a Poly-B–hydroxybutyrate/Calcium polyphosphate channel in bacterial plasma and membranes", Proc. Natl. Acad. Sci. USA, v85, 4176–4180, 1988).*
Rosetta Reusch ("Poly–B–hydroxybutyrate/CAlcium Polyphosphate Complexes in Eukaryotic Membranes", Proceedings of the Society for Experimental Biology and MEdicine, 1989, 191(4), 377–381).*
Tsien et al. ("Calcium Channels: Mechanisms of Selectivity, Permeation, and Block", Ann. Rev. Biophys. Chem. 1987, 16:265–90).*
David Page (Principles of Biological Chemistry, Willard Grant Press, 1976, pp. 180–181).*
Reusch, R.N. et al., J. Bacteriol. 156, 778–788 (1983) Month Unknown.
Reusch, R.N. et al., J. Bacteriol. 168, 553–562 (1986) Month Unknown.
Reusch, R.N., Soc. Exp. Biol. and Med. 19, 377–381 (1989)Month Unknown.
Reusch, R.N. et al., Can. J. Microbiol. 33, 435–444 (1987) Month Unknown.
Reusch, R.N. et al., Proc. National Acad. Science 85, 4176–4180 (1988) Month Unknown.
Reusch, R.N., FEMS Microbiology Rev. 103, 119–130 (1992) Month Unknown.
Hess, P. et al., Nature. 309, 453 (1984) Month Unknown.
Almers, W. et al., J. Physiol. 353, 585 (1984) Month Unknown.
Phospholipid Handbook, Marcel Dekker, Inc., New York 1–22 and 603–637 (1993) Month Unknown.
Hannahan, D., J. Mol. Biol. 166, 557–580 (1983) Month Unknown.
RRC, New Liposomes a Practical Approach, IRL Press, pp. 1 to 104 (1990) Month Unknown.
Tsien, et al., Ann. Rev. Biophys. Biophys. Chem. 16, 265, (1987) Month Unknown.
MacCallum, J.R. et al., Polymer Electrolyte Reviews, Elsevier Applied Science, N.Y. pp. 23–37 (1987) Month Unknown.
Watanabe, et al., Macromolecules 17, 2908–2912 (1984) Month Unknown.
Corbridge, D.E.C., Stud. Inorg. Chem. 6:170–178 (1985) Month Unknown.
Martin, R.B., Bioinorganic chemistry of magnesium In "Metal Ions in Biological Systems", Sigel, H. and Sigel, A., eds., 26:1–13 (1990) Month Unknown.

* cited by examiner

*Primary Examiner*—Nam Nguyen
*Assistant Examiner*—Alex Noguerola

(57) ABSTRACT

Lipid bilayers which incorporate poly-3-hydroxybutyrate/ polyphosphate ion channels. The ion channels are preferably purified polyhydroxybutyrate polyphosphate complexes extracted from organisms or prepared from the individual constituents which have been size selected. The bilayers are useful for testing the affect of various molecules and ions on the channel which correlates to the in vivo result. The bilayers are useful for transporting the channels into cells or other bilayers.

11 Claims, No Drawings

ASSAY METHOD USING POLYHYDROXYBUTYRATE AND POLYPHOSPHATE MEMBRANES WITH CHANNELS

This is a divisional of application Ser. No. 08/317,204 filed on Oct. 3, 1994, "whereas now U.S. Pat. No. 5,585, 249."

BACKGROUND OF THE INVENTION (1) Field of the Invention

The present invention relates to a stable bilayer or multilayer membrane with channels through the membrane and containing a phospholipid and a mixture of a polyhydroxybutyrate (PHB) and a polyphosphate. In particular, the present invention relates to a method for transporting an ion or molecule through the channel in the membrane. Further, the present invention relates to a method for assaying for compounds which block the channel. Finally, the present invention relates to a method for incorporating the channels in membranes.

(2) Description of Related Art

R-poly-3-hydroxybutyrates and inorganic polyphosphates (polypi) are ancient and ubiquitous homopolymers whose biological roles are not well understood. PHB, a head-to-tail polymer of R-3-hydroxybutyrate, is best known as a high molecular weight (60,000 to 1,000,000) polymer deposited within inclusion bodies in many prokaryotes. PolyPi are linear chains of orthophosphate joined by phosphoanhydride bonds, which have a free energy of hydrolysis comparable to that of ATP. Reusch et al (R. N. Reusch and H. L. Sadoff. J. Bacteriol. 156, 778–788 (1983); R. N. Reusch, et al., J. Bacteriol. 168, 553–562 (1986); and R. N. Reusch. Soc. Exp. Biol. and Med. 19, 377–381 (1989)) isolated PHB having a lower molecular weight (<12,000) from bacterial plasma membranes, and from membranes and organelles of plants, and concluded that membrane PHB in *Escherichia coli, Azotobacter vinelandii* and *Bacillus subtilis* was complexed with Ca(polyPi). The presence of these complexes in bacterial membranes is discerned by observing the thermotropic fluorescence of the membrane probe, N-phenyl-1-naphthylamine; dissociation of the complexes gives rise to an increase in fluorescence with a peak at ca 56° C. The concentration of PHB/polyPi is low during log-phase growth, but increases fifty to a hundred fold or more when the cells are made genetically competent whether by physiological or physico-chemical means. At high concentrations, the complexes cause alterations of the plasma membrane structure observable by freeze-fracture electron microscopy (R. Reusch, et al., Can. J. Microbiol. 33, 435–444 (1987)).

Poly-β-hydroxybutyrate (PHB) and calcium polyphosphate complex membranes were extracted as biological complexes from bacterial membranes (Reusch, R., and Sadoff, H., Proc. National Acad. Science 85, 4176–4180 (1988)). Attempts to reconstitute the complex membranes from calcium polyphosphate and PHB in liposomes met with limited success, since they were significantly disassociated as can be seen from FIG. 1 of this reference. The putative functions of the biological complexes are further discussed in FEMS Microbiology Rev. 103, 119–130 (1992).

Reusch and Sadoff proposed a structure for the PHB/Ca (polyPi) in *E. coli,* based on molecular and computer modeling with regard for the physical properties of the polymers, the coordination geometry of calcium, and the membrane environment. It assumes that the amphophilic PHB forms a helical pore—with a lipophilic exterior of methyl and methylene groups and a hydrophilic lining of ester carbonyl oxygens—that is traversed by the more rigid polypi anion. A channel is formed in the space between the two polymers which has solvating carbonyl oxygens column evenly spaced along its outer wall and negatively-charged binding sites at regular intervals along its inner wall. The channel is subdivided into several contiguous parallel lanes through which cations may move in single-file in the direction of concentration or voltage gradients. Since all cation binding sites are identical, the potential energy minima are also identical. This model of a multiple-site, single-file channel is consistent with current views on protein $Ca^{2+}$ channel structure expressed by Hess and Tien and Almers and McCleskey (Hess, P. and R. W. Tsien. Nature. 309, 453 (1984); and Almers, W. and McCleskey, E. W., J. Physiol. 353, 585 (1984)). The model is used as a basis for explaining how the inventors believe the present invention functions; however, they do not want to be bound by any particular theory.

OBJECTS

It is therefore an object of the present invention to provide ion channel complexes in lipid bilayers or multilayers. It is further an object of the present invention to provide a method for forming ion channel complexes in bilayers which is simple and economical. Further still, it is an object of the present invention to provide an assay method for determining whether the channels are blocked by particular ions or molecules. These and other objects will become increasingly apparent by reference to the following description.

DESCRIPTION OF PREFERRED EMBODIMENTS

The present invention relates to a stable bilayer or multilayer membrane which has a channel between a first side and a second side of the membrane which comprises: a bilayer (or bilayers) which separates two aqueous regions on each of the sides of the membrane; and a substantially pure mixture of (1) a polyhydroxybutyrate (PHB) and (2) a polyphosphate, the PHB and the polyphosphate having molecular weights which provide a channel across the membrane.

Further the present invention relates to a method for transporting a cation through a channel which comprises: providing a stable bilayer or multilayer membrane which has a channel between a first side and a second side of the membrane which comprises: a lipid bilayer which separates two aqueous regions on each of the sides of the membrane; and a substantially pure mixture of (1) a polyhydroxybutyrate (PHB) and (2) a polyphosphate, the PHB and the polyphosphate having molecular weights which provide a channel across the membrane; and providing transport means for the cation through the channel.

Further still, the present invention relates to a method for assaying a calcium channel blocking compound which comprises: providing a stable bilayer or multilayer membrane which has a channel between a first side and a second side of the membrane which comprises: a lipid bilayer which separates two aqueous regions on each of the sides of the membrane; and a mixture of (1) a substantially pure polyhydroxybutyrate (PHB); and (2) a polyphosphate, the PHB and the polyphosphate having molecular weights which provide a channel across the membrane; providing the calcium channel blocker compound and calcium ions on one or both sides of the membrane; and providing transport means for the calcium ion through the channel, wherein the calcium channel blocking compound blocks the channel through the membrane.

Finally, the present invention relates to a method for forming a bilayer or multilayer membrane which has a channel between a first side and a second side of the membrane which comprises: mixing a phospholipid with a mixture of an inorganic polyphosphate and a polyhydroxybutyrate (PHB) in an organic solvent to provide a membrane forming solution; and forming a membrane between two aqueous phases, wherein the PHB and inorganic polyphosphate form a channel through a bilayer formed by the phospholipid.

The PHB can be economically extracted, sonicated and purified from prokaryotes to produce a molecular weight between 1,000 to 30,000, preferably 11,000 to 16,000. PHB also occurs in higher organisms; however extraction is more difficult. The PHB can also be chemically synthesized by polymerization using well known processes.

Salts of the polyphosphate besides calcium can be used such as strontium, barium, manganese, magnesium, lithium, sodium, potassium, rubidium or cesium. Such metals are in Group IA and IIA of the periodic table.

The phospholipids are preferably:

(1) 1,palmitoyl-2,oleoylphosphatidylcholine (Avanti Polar Lipids, Birmingham, Ala.);

(2) *E. coli* phospholipids which are mainly phosphatidylethanolamine and phosphatidyl glycerol (4:1 mixture) with mixed fatty acyl chains mainly 16:0, 16:1, 18:1 (Avanti Polar Lipids). Many other synthetic and natural phospholipids can be used and other lipids such as triglycerides, cholesterol and the like can be added. These are described in Phospholipid Handbook, Marcel Dekker, Inc., New York 1–22 and 603–637 (1993).

The PHB and polyphosphate mixture can be dried by any means which does not decompose the PHB. A vacuum oven can be used for instance. A microwave oven can be used. PHB and polyPi can be mixed in a mortar and pestle, heated to the melting point of PHB (ca 175° C.) and cooled slowly. The preferred ratio of PHB to CaPolyPi is between about 1 to 1 and 10 to 1 and most preferably 2:1 PHB to CaPolyPi in about 1% of phospholipid. The ratio of phospholipid to the mixture is between about 1000 to 1 and 100,000 to 1.

The membrane can be formed in any solvent in which the phospholipid, polyphosphate and PHB can be dissolved. Chloroform and dichloromethane have been used successfully. Mixing methods other than sonication can be used. Sonication is preferred.

Preferably, a solution of PHB in chloroform is added to dry pulverized Ca (PPi), the chloroform is evaporated and the mixture is microwaved to dry (4 min) Chloroform (dry) is added and the mixture is sonicated. The chloroform solution is added to the phospholipid in decane and the chloroform is evaporated to make a bilayer. If liposomes are made, phospholipid are added to the chloroform solution. The chloroform is evaporated, aqueous salt buffer is added to the dry film, and the mixture is sonicated.

The aqueous bathing solution for the membrane can be symmetric (same solution on both sides of membrane) or unsymmetric. Buffers are used to maintain the pH, preferably between about 5 and 9. The solutions preferably have a high ionic strength and contain an amount of magnesium salts.

The present invention is useful for assaying for calcium, or other metal, blocking compounds. Inorganic blocker compounds are for instance lanthanum, aluminum, nickel, cadmium, cobalt and manganese. Organic $Ca^{2+}$ blockers are for instance nifedipine, verapamil and diltiazem.

The transport means can be ion concentration or voltage differentials. Preferably the aperture for the experiments with the voltage clamp has a cross-sectional area of between 50 and 1000 square $\mu$m. The bilayer membrane has a thickness of between about 40 and 120 Angstroms.

Usually a bilayer membrane is formed. It will be appreciated that there can be multiple layers formed.

The following are non-limiting examples of the present invention.

EXAMPLE 1

This Example shows the extraction and purification of PHB (about 11,000 to 13,000 average MW) from *Escherichia coli* and the formation of a bilayer membrane complex of PHB and calcium polyphosphate with the channels.

The cells of *E. coli* were made competent by the procedures of Hanahan (Hanahan, D., J. Mol. Biol. 166, 557–580 (1983)) and Reusch (Reusch, et al, Proc. Natl. Acad. Sci., Vol. 85, pp. 4176–4180, (1988)). PHB was extracted from the *E. coli* using hot chloroform (between about 50° C. to reflux) cooled and then filtered to remove insolubles. The PHB is precipitated with five (5) volumes of methanol. The PHB was suspended in 10 mM Tris buffer (tris (hydroxymethylaminomethane)), EDTA pH 8.0 and treated with proteinase K (200 $\mu$g/ml) of 37° C. for 2 hours to remove proteins. The PHB was then collected by centrifugation and washed in sequence with distilled water (3×), methanol (2×) and acetone (2×). The PHB was dissolved in chloroform and precipitated by addition of 5× methanol (2×). The purified PHB had an average molecular weight of about 11,000 to 13,000.

Calcium polyphosphate (Ca(polyPi)) was prepared by adding a molar excess of 1M $CaCl_2$ to an aqueous solution of sodium phosphate glass 45 (Sigma Chemical, St. Louis, Mo.). The precipitate was collected by centrifugation, washed twice with an aqueous $CaCl_2$ solution and dried by freeze-drying and microwaving. The sample was pulverized and then microwaved again.

A chloroform solution of the purified PHB (in a range between 1 to 10 $\mu$g/ml) was added to a small amount of an excess of pulverized Ca(polyPi) (<1 mg). The chloroform was removed with a stream of dry nitrogen and the remaining mixture was heated in a microwave oven at full power two periods of two (2) minutes. Dry chloroform was added and the mixture was sonicated at medium (30% of full power) power (30% pulse time) for two (2) minutes) using a VIBRA CELL ULTRASONICATOR (Sonics and Materials, Danbury, Conn.). A portion of the filtered supernatant was added to a solution of (1-palmitoyl-2, oleoyl-phosphatidylcholine (POPC)) as the phospholipid (PL) in decane. Preferred was 10 ng PHB for 40 $\mu$g PL (40,000 ng) which is 0.025%. A percentage range of 0.1% to 0.001% can be used. The chloroform was then evaporated.

The mixture of the membrane complex was used to form a bilayer across a 250 $\mu$meter aperture in a nylon (DELRIN, Dupont, Wilmington, Del.) cuvette separating to aqueous bathing solutions containing symmetric solutions of 250 mM $CaCl_2$, 1 mM $MgCl_2$ in 10 mM Tris(tris (hydroxymethylaminomethane)) HEPES (4-(2-hydroxyethyl)-1-piperazine sulfonic acid) at a pH of 7.3 at room temperature (20° C.–24° C.).

The membrane formed was tested in a cell using the voltage clamp technique. A voltage was applied to one side (cis). The trans side was taken as ground. The voltage applied was between 60 mV and 120 mV. The voltage was held constant and the current was measured. The system measured the current necessary to maintain voltage. The results were that there was single channel activity which was voltage-dependent. Calcium ion moved to the trans side of the cell. The cell can thus be used to test the effectiveness of calcium channel blockers.

EXAMPLE 2

This example shows calcium channels prepared from purified PHB isolated from *E. coli* and separated in a chromatographic column to obtain an average molecular weight between 8,000 and 15,000 and then mixed with synthetic calcium polyphosphate.

*E. coli* DH5α were made competent and the cell pellet was washed as described in Example 1. The PHB was then extracted with hot chloroform. The PHB was precipitated with 5×volume of methanol, suspended in Tris, EDTA buffer, pH 7.5 and incubated overnight with proteinase K (200 μg/ml) at 37° C. The PHB was collected by centrifugation, and washed sequentially with distilled water (2×), methanol (2×) and acetone (2×). The purified polymer was then dissolved in chloroform and precipitated from solution with 5× volume of methanol. The polymer was redissolved in chloroform, filtered, and then chromatographed on a non-aqueous size exclusion column (SHODEX K-803, Waters, Milford, Mass.), and the PHB was detected by UV absorption at 245 nm. The absorption detected the change in refractive index effected by the polymer as a function of molecular weight.

Calcium polyphosphate was prepared by dissolving sodium polyphosphate glass (average chain length 45; Sigma Chemical Col., St. Louis, Mo.) in distilled water and adding an excess of calcium chloride. The calcium polyphosphate precipitate was collected by centrifugation, dried and pulverized.

As in Example 1, a solution of the PHB in chloroform (10 μg/ml) and phospholipid in chloroform was added to an excess (ca 1 mg) of calcium polyphosphate. The chloroform was evaporated with a stream of nitrogen gas and the polymer mixture was dried by heating at full power in a microwave oven (2×2 min). Dry chloroform was added and the mixture was sonicated at low power (30%) for 2 minutes while maintaining a low temperature (from 4° C. to 15° C.). The supernatant was filtered and added to the phospholipids as in Example 1. The results using the voltage clamp technique were single-channel currents.

EXAMPLE 3

This example shows calcium channels prepared from mixed molecular weight PHBs from inclusion bodies in bacteria and synthetic calcium polyphosphate.

PHB from Alcaligenes species was purchased from Sigma channels. The polymer was purified and sonicated and chromatographed on a non-aqueous size-exclusion column as described in Example 2. The fraction eluting in the same time interval as *E. coli* PHB was collected and used for the preparation of calcium channels as described in Example 2. The results in the voltage clamp cell were the same as in Example 2.

Comparative Example 4

As described in Reusch et al in Proc. Natl. Acad. Sci 85, 4176–4180 (1988), the channel complexes were isolated from the bacteria and used to form the bilayer. The problem with this approach was that there are other biological materials, such as proteins and lipopolysaccharides, which modify the channel characteristics.

*Escherichia coli* were made genetically competent essentially by the procedure of Hanahan (J. Mol. Biol. 166, 557–580 (1983)) as previously described (Reusch et al, J. Bacteriol. 168, 553–562 (1986)). In order to extract the membranes, the cells were collected by centrifugation, washed, sequentially with methanol, methanol:acetone (1:1) and then acetone, and then extracted overnight with chloroform (ca 0.5 ml chloroform per 100 ml cells). All solvents were dry and all procedures carried out at 4° C., in a dry environment. A portion of the chloroform solution (between 10 μl to 200 μl) was added to a solution of 1-palmitoyl, 2-oleoyl, phosphatidylcholine (POPC) in decane (20 μl of 40 mg/ml). The chloroform was removed with a stream of dry nitrogen gas, and the lipid mixture was used to paint a bilayer across a 250 μm aperture in a (DELRIN) cuvette separating two aqueous bathing solutions containing symmetric solutions of 250 mM $CaCl_2$, 1 mM $MgCl_2$, in 10 mM Tris HEPES, pH 7.3 as in Example 1. This bilayer was effective for evaluation purposes. The results using the voltage clamp technique were channels were observed at voltages between 60 mV and 100 mV. They were voltage-gated and voltage-dependent, although this was not known at the time.

EXAMPLE 5

This Example shows the preparation of purified calcium channels from *E. coli* using a chromatographic column. It was unexpected that the channel could be preserved using this method of purification.

*E. coli* DH5a were made competent essentially by the method of Hanahan as previously described by Reusch et al (1986). The cells were collected by centrifugation at low speed (1500 rpm) at 4° C. for 15 minutes. The cell pellet was washed sequentially with methanol (2×), methanol:acetone (1:1) (2×) and acetone (2×), dried and then extracted overnight with chloroform. All solvents were dry and cold. All procedures were carried out at low temperature in a dry atmosphere. The extract was filtered with a TEFLON (Dupont, Wilmington, Del.) syringe filter (0.20 μm) and chromatographed on a non-aqueous size-exclusion column (Shodex K-803, (8 mm×25 cm) Waters, Milford, Mass.), using chloroform as eluent. The fraction that eluted in the molecular weight range of 17,000±4,000 was found to have single-channel calcium channel activity when it was incorporated into a planar lipid bilayer, composed of 1-palmitoyl-2,oleoyl-phosphatidylcholine (POPC) as in Example 1. The complex was examined by the voltage-clamp techniques of Example 1. Analysis of this faction showed it contained PHB, polypi and calcium, but no protein. This purified channel extract was also incorporated into liposomes composed of the above lipid and transferred into the planar lipid bilayer as in Example 1. The results using the voltage clamp technique were single-channel currents that were voltage-dependent.

EXAMPLE 6

This example shows the incorporation of purified extracted complexes into liposomes using sonication.

PHB/polyPi complexes were extracted and purified from *E. coli* as in Example 5. A portion of the chloroform extract (diluted between 1 to 100 μl) was added to a solution of phospholipid in chloroform. The phospholipids were 1-palmitoyl, 2-oleoyl phosphatidylcholine (POPC), or a 1:1 mixture of bovine brain phosphatidylethanolamine (PE) and bovine brain phosphatidylserine (PS) (Avanti Polar Lipids, Birmingham, Ala.), or a 2:1 mixture of POPE and POPG (PG=phosphatidylglycerol). The chloroform was evaporated with a stream of nitrogen forming a thin film of the lipid mixture. A buffer (e.g. 10 mM KHepes, pH 6.4 containing 10 mM $CaCl_2$, 45 mM $MgCl_2$, 100 mM KCl) was added and the sample was placed in a sonication bath for 30 min at 4° C. and kept in an inert atmosphere (nitrogen or argon). The phospholipid dispersion was centrifuged at 80,000 g for 30 min at 4° C. and the supernatant was applied to a 1×15 cm Sepharose 4B (Pharmacia, Piscataway, N.J.). Fractions were collected and tested for the presence of complex by adding the hydrophobic probe, N-phenyl-1-naphthyl amine, and observing the thermotropic fluorescence. The complex gives rise to a fluorescence peak at ca 56° C. Fractions containing the complex was added to the aqueous bathing solution (cis side) of the voltage-clamp planar bilayer system described in Example 1 and channel activity was observed indicating that the complex from the liposomes had been incorporated into the bilayer.

Many different methods can be used for forming liposomes and the liposomes may be unilamellar or multilamellar, small or large. They can be formed from many different phospholipids and mixtures thereof and may also include other lipids such as cholesterol and triglycerides. The techniques are well established (see RRC New. Liposomes a Practical Approach, IRL Press, pages 1 to 104 (1990)). The complexes constituted from purified PHB and Ca(polyPi) (or other polypi salt) can be incorporated into any of these liposomes by simply adding a portion of the chloroform solution of the complexes to a chloroform solution of the lipids, evaporating the solvent, and forming the liposomes from the remaining lipid film. The aqueous medium in which the liposomes are "dissolved" should preferably be of high ionic strength with a pH between 6 and 8. It should preferably contain salt(s) of one or more of the following: $Ca^{2+}$, $Sr^{2+}$, $Ba^{2+}$, $Mn^{2+}$, $Mg^{2+}$, $Li^+$, $Na^+$, $K^+$, $Rb^+$ or $Cs^+$.

EXAMPLE 7

The exterior membranes of frog are oocytes and are coated with the complex incorporated in liposomes. The channel forms by itself. This provides a channel into the oocytes for the testing of various chemicals.

Comparative Example 8

The procedure of Reusch et al, Proc. National Acad. Science 85, 4176–4180 (1988) was repeated with PHB with Ca poly (P)) as set forth at page 4178 of this reference in an attempt to prepare a liposome. In this case the complexes were unstable. The problems of forming liposomes with stable complexes was thus not solved in this reference.

EXAMPLE 9

E. coli were used as a source of PHB/polyPi complexes because they do not synthesize high molecular weight cytoplasmic PHBs which coextract with and are difficult to separate from the smaller membrane PHBs. E. coli DH5α were made competent by a variation of the method of Hanahan as previously described in Example 1, and the complex was extracted from the delipidated dried cell residue into chloroform and purified chromatographically as in Example 5. Since the complex is very labile and sensitive to moisture, all steps of the isolation procedure were conducted at 4° C. in a dry atmosphere of nitrogen. As in Example 1, the purified extract was added to a solution of synthetic 1-palmitoyl, 2-oleoyl phosphatidylcholine (Avanti Polar Lipids, Birmingham, Ala.) in decane (20 mg/ml), and the chloroform as removed with a stream of dry nitrogen. The remaining decane solution was used to form a bilayer across a 150–250 µm aperture between two aqueous bathing solutions.

The complex between the two linear homopolymers of PHB and polypi is believed to be symmetrical, with the anionic polypi oriented perpendicular to the membrane. The cis side of the bilayer, arbitrarily defined as the inside, was of variable potential, while the trans side or outside was kept at virtual ground. Voltages are reported in the usual convention of inside minus outside.

When holding potentials greater than +60 mV were maintained for several minutes across a bilayer containing PHB/PolyPi between symmetric solutions composed of 10 mM HEPES, pH 7.5 and 250 mM of either $CaCl_2$, $SrCl_2$ or $BaCl_2$ at room temperature, stepwise current fluctuations were observed. Bursts containing well-defined current steps lasting from a few seconds to several minutes alternating with periods of inactivation of 10 seconds to several minutes continued for 15 to 60 minutes. A given cell extract, stored dessicated at 4° C., could be used to produce channel activity for two weeks, but activity was lost in a few minutes when the complex-containing extract was exposed to room air. The current fluctuations at +100 mV were ca 1 pA with $Ca^{2+}$ and $Sr^{2+}$, and $Ba^{2+}$. $Mg^{2+}$ was permeant in the absence of $Ca^{2+}$, but $Ca^{2+}$ strongly selects against $Mg^{2+}$, however, low concentrations of $Mg^{2+}$ stabilized the channel. The ability of $Sr^{2+}$ and $Ba^{2+}$ to substitute for $Ca^{2+}$ and the selectivity against impermeance of $Mg^{2+}$ are characteristic of $Ca^{2+}$ channels (Tsien, et al, Ann. Rev. Biophys. Biophys. Chem. 16, 265 (1987).

Single channel current-voltage relationships for the permeant cations in symmetric solutions were linear from 40 mV to 120 mV. Below 40 mV the single-channel currents were too small and brief to measure, and at potentials above +100 mV the open current noise increased appreciably. The single-channel conductances were ca 10 pS for $Ca^{2+}$, $Sr^{2+}$ and $Ba^{2+}$. These conductances were not significantly altered when concentrations of the carrier cations was reduced to 100 mM indicating that carrier sites in the channel were saturated with respect to the carrier cation, and that the relative conductances reflect relative rates of cation transport. The channel open times were influenced by both the voltage and the nature of the cation carrying the current. As voltage approached the reversal potential (zero for the symmetric solutions), open times decreased substantially for each of the permeant cations. In the absence of $Ca^{2+}$, monovalent cations were permeant.

The channel was selective for divalent cations over monovalent cations. The selectivity of the channel is shown when a 250 mM $SrCl_2$ solution was replaced on the trans side by an isotonic solution of 8 mM $SrCl_2$ and 270 mM KCl. The reversal potential of −37 mV was essentially the same as the equilibrium potential calculated from the Nernst equation, whereas that for $Cl^-$ was +9 mV and that for $K^+$ was nominally infinity.

In many types of cells, $Ca^{2+}$ currents are blocked by a variety of transition metals, presumably because they compete with $Ca^{2+}$ for binding sites in the channel. Lanthanum, cobalt and cadmium were found to be to be impermeant in the channel complex. Both reduced the single channel current in a concentration dependent manner, with the order of effectiveness $La^{3+}$>Co>Cd.

The channel extract was chromatographed further on a non-aqueous size exclusion column (Shodex K803), and eluent fractions examined for single-channel current activity in nonsymmetric solutions, cis was 20 mM $BaCl_2$ in 10 mM Hepes, pH 7.3, 60 mM RbCl, trans was 5 mM $MgCl_2$, 60 mM RbCl, 10 mM Hepes, pH 7.3 at −1009 mV. The fraction with channel activity eluted in a relatively sharp peak in a molecular weight range defined as 17,000±4,000 by standards of polyisoprenes (Polysciences, Warrington, Pa.) and PHB synthetic (Seebach, ETH, Zurich). The fraction with channel activity contained PHB and polypi, but no protein or nucleotides. The single channel conductance of the purified complex was unchanged, but it was more labile, suggesting that stabilizing substance(s) were removed by the chromatography.

EXAMPLE 10

The channel composition was confirmed by preparing PHB/Ca(polyPi) in vitro from purified PHB isolated from competent *E. coli* DH5α and Ca(polyPi) prepared from $CaCl_2$ and sodium phosphate glass as in Example 1. Dry pulverized Ca(polyPi)(100 µg) was added to a solution of PHB in chloroform (10 µg/ml) and the mixture was ultrasonicated. The filtered solution was added to lipids and a bilayer was formed as described in Example 9. It is expected that this channel will have the same characteristics as the channels extracted from *E. coli*.

In reference to the Examples, the aqueous bathing solutions for the membrane can be symmetric (some composition on both sides of the membrane) or unsymmetric (different compositions). The solution(s) can contain salts of calcium, strontium, barium, manganese, magnesium, lithium, sodium, potassium, rubidium and cesium (Periodic Table, Groups IA and IIA). Preferably magnesium, can be provided in the solution and can pass through the channel. The solution(s) can contain buffers to maintain the pH, preferably between 5 and 9 to maintain membrane. The solutions usually have a high ionic strength (high concentration of ions).

The PHB/PolyPi channel complex may be viewed as a single molecule of an ion-conducting polymeric electrolyte positioned across a membrane (MacCallum, J. R. and Vincent, C. A., Polymer Electrolyte Reviews, Elsevier Applied Science, N.Y. pp. 23–37 (1987). PHB shares the molecular characteristics common to salt-solvating polymers. Its ester carbonyl oxygens have sufficient electron donor power to form weak coordinate bonds with cations, and the inter and intrachain distance between carbonyl oxygens in the proposed structure permits multiple bonds between the polymer chain and the cation. In addition, the polymer is above its glass temperature (ca 0° C.) under physiological conditions so that bond rotation and segmental motions of the polymer chain may aid in the transfer of cations from site to site. The backbone structure of PHB is identical to that of the polyester, poly-β-propiolactone, which was reported by Watanabe et al (Watanabe et al, Macromolecules 17, 2908–2912 (1984)) to form ion conducting complexes with lithium perchlorate and iron chloride. The salts solvated by this class of polymers are generally composed of cations with high solvation energies and large anions with diffuse charge. $Ca^{2+}$ and polypi share these characteristics—the energy of hydration of calcium is −397 kcal/mol, and each polypi monomer unit shares its single negative charge distributed between two oxygens.

Selectivity is accomplished by exploiting the individual and combined molecular properties of the two polymers to discriminate among cations by ion size, binding energy, hydration energy, and coordination geometry. The negatively-charged phosphoryl residues of polypi attract cations to the mouth of the channel, and the flexibility of the polypi chain and the distance between adjacent negative charges favor the sequestration of divalent cations in the presence of large concentrations of monovalent cations (Corbridge, D. E. C., Stud. Inorg. Chem. 6:170–178 (1985)). PHB provides a second selectivity filter by preferentially solvating cations with coordination geometries that conform to the spatial arrangement of the ester carbonyl oxygens. Jointly, the oxygen ligands of PHB and polypi define an equilibrium cavity that will determine the optimal cation size.

The preceding mechanism of ion permeation is consistent with the selectivity order and single-channel conductance of the channel. If it is assumed that the ligand geometry is optimal for $Ca^{2+}$, then $Sr^{2+}$ and $Ba^{2+}$ which have similar coordination geometries would also be permeant; however, we would expect that significantly increasing the cation diameter would distort the equilibrium cavity and weaken binding. This is compatible with the experimental selectivity order $Ca^{2+}=Sr^{2+}>Ba^{2+}$, and the conductance order $Ba^{2+}>Sr^{2+}=Ca^{2+}$. Exclusion of $Mg^{2+}$ is expected due to its small size, different coordination geometry, and slow rate of water exchange (Martin, R. B., Bioinorganic chemistry of magnesium. In "Metal Ions in Biological Systems", Sigel, H. and Sigel, A., editors 26:1–13 (1990)). Ions that bind tightly to polyPi at the channel face, but are inhibited from entering by size, as $La^{3+}$, or coordination geometry, as $Cd^{2+}$ or $Co^{2+}$, block the entry of permeant cations. Permeant blockers like $Mn^{2+}$ bind more tightly than $Ca^{2+}$ and move through the channel more slowly, inhibiting the $Ca^{2+}$ current.

Despite the simplicity of its composition and structure, the complex exhibits many of the characteristics of eukaryotic $Ca^{2+}$ channels, and thus serves as a model to elucidate the structural features and molecular mechanisms underlying ion transport in these more elaborate systems.

EXAMPLE 11

This example shows calcium channels prepared from purified PHB, isolated from *E. coli*, and incorporated in a bilayer of phospholipid and synthetic calcium polyphosphate added to the aqueous solution surrounding the bilayer.

*E. coli* DH5α were made competent and the cell pellet washed and treated with proteinase K as in Example 2. The PHB in chloroform was added to 1-palmitoyl, 2-oleoyl phosphatidylcholine in decane (10 ng PHB to 40 µg lipid). The chloroform was evaporated and a bilayer was formed with the PHB lipid solution between two aqueous bathing solutions of 100 mM $CaCl_2$, 1 mM $MgCl_2$ in 10 mM Tris HEPES, pH 7.4. Calcium polyphosphate was prepared as described in Example 1 and added to the aqueous bathing solution. A voltage of 60 mV was applied to the inside. The result was single channel activity which was voltage dependent. The PHB alone at this concentration in the aqueous solution has no channels under these conditions. After the application of the voltage to the solution with $CaCl_2$ the channels are formed.

It is intended that the foregoing description be only illustrative of the present invention and that the present invention be limited only by the hereinafter appended claims.

I claim:

1. A method for transporting a cation through a channel in a membrane in an assay which comprises:

(a) providing an assembled stable bilayer or multi layer membrane having a first side and a second side and the channel therethrough, wherein the membrane separates two aqueous regions such that there is one of the regions on each of the sides of the membrane, wherein the membrane exhibits single channel current-voltage relationship ratios between 40 mV and 120 mV for $Ca^{+2}$, $Sr^{+2}$, and $Ba^{+2}$ when an identical solution is present in the two aqueous regions, and wherein the membrane comprises:

a phospholipid bilayer or multilayer produced from isolated phospholipids which separates the two aqueous regions; and one or more channels produced from a substantially pure mixture of (1) an isolated polyhydroxybutyrate (PHB) and (2) an isolated polyphosphate, the PHB and the polyphosphate each having molecular weights which allow the formation of the channel across the phospholipid during assembly of the membrane; and (b) providing transport means for transporting the cation through the channel in the membrane in the assay.

2. The method of claim 1 wherein the cation is selected from the group consisting of an element and a molecule which is ionic and the transport means is an electrical potential or a concentration difference between the sides of the membrane.

3. The method of claim 1 wherein the phospholipid biliyer or multilayer is 1-palmityl, 2-oleoyl-phosphatidylcholine.

4. The method of claim 1 wherein the PHB has a molecular weight between about 1000 and 30,000 daltons.

5. The method of claim 1 wherein the weight ratio of the phospholipid bilaver or multilayer to the mixture of the PHB and the polyphosphate is between about 1000 to 1 and 100,000 to 1 and the ratio of PHB to polyphosphate is between about 1 to 1 and 10 to 1.

6. The method of claim 1 wherein the membrane is supported in an aperture through a plate.

7. The method of claim 6 wherein the aperture has a cross-sectional area of between about 50 and 500 square $\mu$m.

8. The method of claim 1 wherein the polyphosphate is metal polyphosphate and the metal is selected from the group consisting of lithium, sodium, potassium, rubidium, cesium, calcium, strontium, barium and manganese.

9. The method of claim 1 wherein a metal ion selected from the group consisting of lithium, sodium, potassium, rubidium, cesium, calcium, strontium, barium and manganese is transported through the channel by the transport means.

10. The method of claim 1 wherein the membranes a bilayer membrane having a thickness between about 40 and 120 $\mu$m.

11. The method of claim 1 wherein the membrane is a bilayer membrane which is supported in an aperture through a plate, the aperture having a cross-sectional area between about 50 and 500 square $\mu$m and with the bilayer membrane having a thickness between about 40 and 120 $\mu$m.

* * * * *

UNITED STATES PATENT AND TRADEMARK OFFICE
CERTIFICATE OF CORRECTION

PATENT NO. : 6,602,398 B1
DATED : August 5, 2003
INVENTOR(S) : Rosetta N. Reusch It is certified that error appears in the above-identified patent and that said Letters Patent is hereby corrected as shown below:

Column 1,
Line 25, "(polypi)" should be -- (polyPi) --.

Column 2,
Line 3, "polypi" should be -- polyPi --.
Line 14, "Hess and Tien" should be -- Hess and Tsien --.

Column 3,
Line 53, "(4 min)" should be -- (4 min). --.

Column 6,
Line 35, "DH5a" should be -- DH5α --.
Line 54, "polypi" should be -- polyPi --.

Column 7,
Line 31, "polypi" should be -- polyPi --.

Column 8,
Lines 9 and 10, "polypi" should be -- polyPi --.
Line 64, "found to be to be impermeant" should be -- found to be impermeant --.

Column 9,
Lines 11, 62 and 64, "polypi" should be -- polyPi --.

Column 10,
Lines 3, 5 and 12, "polypi" should be -- polyPi --.

UNITED STATES PATENT AND TRADEMARK OFFICE
CERTIFICATE OF CORRECTION

PATENT NO. : 6,602,398 B1
DATED : August 5, 2003
INVENTOR(S) : Rosetta N. Reusch It is certified that error appears in the above-identified patent and that said Letters Patent is hereby corrected as shown below:

Column 11,
Line 28, "biliyer" should be -- bilayer --.
Line 29, "palmityl" should be -- palmitoyl --.

Column 12,
Line 20, "membranes" should be -- membrane --.

Signed and Sealed this

Sixth Day of January, 2004

JAMES E. ROGAN
*Director of the United States Patent and Trademark Office*